United States Patent [19]

Williams et al.

[11] Patent Number: 4,927,676

[45] Date of Patent: May 22, 1990

[54] METHOD FOR RAPID ADHERENCE OF ENDOTHELIAL CELLS ONTO A SURFACE AND SURFACES PREPARED THEREBY

[75] Inventors: Joel L. Williams; David B. Montgomery, both of Cary; Lillian P. Baldwin, Durham, all of N.C.

[73] Assignee: Becton, Dickinson and Company, Franklin Lakes, N.J.

[21] Appl. No.: 340,190

[22] Filed: Apr. 19, 1989

Related U.S. Application Data

[63] Continuation of Ser. No. 214,240, Jul. 1, 1988, abandoned.

[51] Int. Cl.$^5$ .............................................. A01N 1/02
[52] U.S. Cl. .................................... 428/36; 427/2; 427/38; 427/39; 427/230; 427/330; 427/372.2; 427/402; 428/64; 428/364; 428/423.1; 428/480; 428/523; 435/174; 435/240.1
[58] Field of Search ................ 428/36, 364, 64, 423.1, 428/480, 523; 427/2, 38, 39, 230, 330, 372.2, 402

[56] References Cited

FOREIGN PATENT DOCUMENTS 0206025 4/1986 European Pat. Off. .

Primary Examiner—Bernard Pianalto
Attorney, Agent, or Firm—Richard E. Brown

[57] ABSTRACT

Small diameter plastic tubing is plasma-treated on the lumen wall and endothelial cells are adhered thereto to give antithrombogenic small diameter conduits useful for vascular grafts and other articles intended to come in contact with blood.

21 Claims, No Drawings

METHOD FOR RAPID ADHERENCE OF ENDOTHELIAL CELLS ONTO A SURFACE AND SURFACES PREPARED THEREBY

This application is a continuation of application Ser. No. 214,240, filed July 1, 1988, now abandoned.

BACKGROUND OF THE INVENTION

1. Field of the Invention

This invention relates to a method for attaching cells to a surface, and more specifically relates to a method for depositing a layer of endothelial cells on a polymeric surface and to surfaces prepared thereby.

2. Background of the Invention

Extensive investigations have been undertaken over many years to find materials that will be biologically and chemically stable toward body fluids. This area of research has become increasingly important with the development of various objects and articles which can be in contact with blood, such as artificial organs, vascular grafts, probes, cannulas, catheters and the like.

Synthetic plastics have come to the fore as preferred materials for such articles. However, such materials have the major drawback of being thrombogenic. Even such plastics as polytetrafluoroethylene and the silicone rubbers which are more compatible with blood than most plastics, still show thrombogenic characteristics.

Thrombogenicity has conventionally been counteracted by the use of anticoagulants such as heparin. Exemplary of heparinization procedures are the disclosures in U.S. Pat. No. 4,613,517 to Williams et al. and U.S. Pat. No. 4,521,564 to Solomon et al.

Over the past three decades, artificial grafts have been used to restore blood flow to areas of ischemia, to provide blood flow for hemodialysis patients and for repair of arterial aneurysms. While these procedures are generally initially successful, long term prognosis for patients receiving such grafts is not encouraging, principally because small diameter grafts (4 mm or less) become occluded over time due to fibrin deposition and cellular adhesion due to the thrombogenic nature of the graft material.

The ideal blood-surface interface has long been considered to be the naturally occurring human endothelium, and much current research is focused on endothelialization procedures. Madri et al. in the *Journal of Cell Biology* 97, 153 (1983) reported that when cells are grown on interstitial collagens, they undergo proliferation and form a continuous cell layer. Williams et al., *Journal of Surgical Research* 38, 618 (1985) described pretreatment of prosthetic graft material with fibronectin, collagen or blood plasma, and reported that essentially no adherence occurred on untreated graft material, but that dramatic increases in adherence occurred on protein-coated polyester grafts. A similar study by Jarrell et al. (*Annals of Surgery*, 203, 671 (1986)) showed a high percentage of firm adherence of endothelial cells to polyester coated with platelet-rich-plasma in 10 min., to amnion/collagen coated polyester in 30 min. and to plain polyester in two hours, but that only the amnion/collagen coated surface exhibited complete graft coverage.

In recent years, attention has focused upon the poor results generally obtained with small diameter vascular grafts. van Wachem et al., in *Biomaterials* 6, 403 (1985) reported clinical success with polymeric grafts of greater than 4 mm, but that grafts of less than 4 mm gave generally disappointing clinical results due to immediate occlusion. Likewise, Baker et al., in *American Journal of Surgery* 150, 197 (1985) stated that long term patency of large diameter vascular grafts is relatively acceptable, but small diameter (less than 4 mm) grafts exhibit poor long-term patency rates.

Seeding of 4 mm inside diameter polyester vascular grafts with endothelial cells and patency after implantation in dogs is discussed by Belden et al. in *Trans. Am. Soc. Artif. Intern. Organs.* 28, 173 (1982).

Modification of polymeric surfaces by treatment with a variety of plasmas to achieve certain results is well known. For example, surface wettability, static properties and receptivity of a surface to deposition of a layer of an adherent polymeric material have been described. The doctoral thesis of Lee M. Smith, "Cell Adhesion As Influenced By Substrate Surface Properties", Department of Material Science and Engineering, the University of Utah, 1978, p. 67, suggests that cell adherence is a function of the carbon/oxygen ratio of the surface. van Wachem et al., (supra) discloses that endothelial cells can be cultured on glass or glow-discharge treated polystyrene.

U.S. Pat. No. 4,452,679 to Dunn et al. discloses a method to modify a polymeric surface to introduce specific chemical groups by treatment of the surface with a plasma in which at least one of the neutral, positive or negative species of the plasma is excluded from contacting the surface.

Applicants are also aware of a disclosure that endothelial cells adhere partially, but not confluently, to an untreated Dacron TM polyester surface, that this surface will become confluently covered in 24 hours, and that near confluent coverage occurs with a Dacron TM surface pretreated with a protein, such as platelet rich plasma. In the present disclosure, the term confluent is used to describe a surface which is substantially covered with cells which are contiguous in all directions.

In spite of the extensive investigations on antithrombogenic prosthetic devices, the problem of thrombogenicity has not been satisfactorily solved, in particular with respect to small diameter grafts. It is toward the solution of this problem that the current invention is directed.

SUMMARY OF THE INVENTION

One aspect of the invention is a method to prepare a surface having a confluent layer of endothelial cells thereon. A substrate is exposed to a plasma generated from a material which includes nitrogen. The plasma treatment causes bonding of amino groups to the substrate. The substrate containing amino groups is contacted with endothelial cells which adhere to the substrate. The density of cells in the contacting medium is sufficient to cause the adhering cells to form a confluent layer on the substrate without cell proliferation. The preferred substrate is polymeric.

Another aspect of the invention is an antithrombogenic article comprising a plasma-treated substrate having a confluent layer of adhered endothelial cells thereon. The articles are preferably polymeric and may be of any shape. The preferred article is a conduit having an inside diameter of 0.5 mm or greater. One preferred, specific embodiment is a conduit having an inside diameter about 2 to 6 mm. The lumen wall of these conduits is plasma-treated and endothelialized.

The plasma may be generated from any source of nitrogen which can be ionized. Preferred plasmas are generated from ammonia, most preferably ammonia containing a low concentration of oxygen.

The plasma treated substrate may be contacted with the endothelial cells in a suitable medium, such as a buffered saline, preferably under incubating conditions, to cause formation of an adhering confluent layer of the cells on the substrate.

Thus, in accordance with the invention articles having a plasma-treated polymeric surface and a confluent layer of adherent epithelial cells thereon are prepared by a two-step method which includes pretreatment of the article surface with a plasma to give an amine-rich surface and application of endothelial cells thereto. The plasma-treated surface prior to endothelialization is stable indefinitely and thus has a long shelf-life. Since the cells adhere quickly and become confluent without cell proliferation, a prosthetic device having the plasma-treated surface of the invention may be removed from stock, endothelialized, and be ready for implantation within minutes of procurement of sufficient cells. The advantages of speed to a patient undergoing surgery are apparent.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

One aspect of the present invention is a method for irreversibly modifying the surfaces of organic and inorganic substrates. More particularly, in accordance with the present invention, the surfaces of organic and inorganic substrates are irreversibly modified by bonding specific chemical functional species onto the surface of the substrate by contacting such surfaces with a plasma of a vaporized material in order to facilitate cell deposition and adherence.

The present invention can be employed to alter the surfaces of solid polymeric materials, including natural and synthetic addition and condensation polymers. Such polymeric materials include, but are not limited to, polyolefins, such as polyethylene, polypropylene, polyisobutylene and ethylene-alphaolefin copolymers, acrylic polymers and copolymers, such as polyacrylate, polymethylmethacrylate, polyethylacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; natural and synthetic rubbers, including butadiene-styrene copolymers, poly-isoprene, synthetic polyisoprene, polybutadiene, butadiene-acrylonitrile copolymers, polychloroprene rubbers, polyisobutylene rubber, ethylene-propylenediene rubbers, isobutylene-isoprene copolymers and polyurethane rubbers; polyamides, such as Nylon 66 and polycaprolactam; polyesters such as polyethylene terephthalate, alkyd resins; phenol-formaldehyde resins; urea-formaldehyde resins, melamine-formaldehyde resins; polycarbonates; polyoxymethylenes; polyimides; polyethers; epoxy resins, polyurethanes; wool; cotton; silk; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Inorganic materials, the surfaces of which can be modified in accordance with the invention, include, but are not limited to, nonmetals, such as graphite; metals, such as iron, aluminum, tin, copper and nickel; metal and other elemental oxides; such as magnesium oxide, silica, alumina and titania; minerals, such as clay, pyrite and asbestos; salts, such as sodium chloride and calcium carbonate; and such synthetic compositions as glass and refractories.

The substrates, whether organic or inorganic, may be any shape, relatively flat or curved, and may be of any composition, such as continuous or particulate, porous or impervious, and large or small. The invention can be employed for altering the surfaces of crystals, powders, plates, strips, films, sheets, wire, fibers, fabrics, filaments, tubing, and cast, extruded or compressed articles, and the like.

For most plasma treatments in accordance with the present invention, a conventional plasma generator may be used. Such generators may include thermal, radio frequency, direct current, audio frequency, and microwave plasmas using internal and external capacitive coupling, inductive coupling, resistive coupling, and waveguide techniques. Electrical excitation may be provided by means of a DC or low frequency AC glow discharge produced by internal electrodes or coupling using inductive or capacitive means with higher frequency power sources from audio frequencies up through radio frequency and into microwave frequencies. Microwave waveguide techniques may also be used. Exemplary of suitable plasma generators are the plasma reactors made by Branson/IPC and plasma surface treatment systems made by Plasma Science Inc.

For the preferred embodiment of the invention wherein a small diameter conduit is treated with plasma, an apparatus as disclosed in a co-pending application filed on even date herewith, now U.S. Pat. No. 4,846,101 may preferably be used. This co-pending application, of common assignee with the present invention, is herein incorporated by reference.

The plasma may be generated from any gas or gaseous mixture which provides reactive functional groups from the gas grafted onto the surface. Suitable gases are, for example, oxygen, nitrogen and low molecular weight organic or inorganic compounds of oxygen or nitrogen such as methanol, acetonitrile or hydrogen cyanide. Preferred gases are nitrogenous such as nitrogen, aliphatic amines of from 1 to 6 carbon atoms, hydrazine, ammonia or mixtures thereof. Other components may be present in the gas mixture such as are hydrogen, halogen and inert gases such as helium, oxygen, neon, krypton and xenon.

The preferred plasma for surface modification in preparation for cell adherence is generated from ammonia containing a low concentration of oxygen. The oxygen to ammonia ratio may be from about 0.005 to 0.8, preferably from about 0.01 to 0.1. The desired ratio may be achieved by bleeding appropriate quantities of the gases into the reaction chamber after conventional pumpdown. However, for most surface treatments in accordance with the present invention, sufficient oxygen remains in the vacuum chamber after pumpdown to achieve the desired ratio. It is evident that the quantity of oxygen remaining in the chamber is related to the pumpdown pressure in the evacuated chamber. Thus a desired oxygen-nitrogen ratio within an appropriate total gas pressure may be obtained by evacuating the chamber to a pre-determined pressure and bleeding in the required amount of ammonia. In general, a close approximation of the desired oxygen concentration can be achieved merely by control of the pumpdown time.

Plasma generation for surface modification in accordance with the present invention may be carried out with a wide range of power settings, radio frequencies, durations of exposure, temperatures, and gas pressures. Ranges for these parameters which provide advantageous results are measured DC or AC power density levels of from 0.001 to 400 watts per cubic centimeter, oscillation frequencies up to 100 megahertz, 2 seconds to 12 hours, 0° to 200° C., and 0.01 to 100 torr. Preferred ranges for these parameters are 0.01 to 200 watts per cubic centimeter, 5 to 30 megahertz, 5 seconds to 120 minutes, 10°-50° C., and 0.01 to 20 torr. Gas flow rates may vary from stagnant conditions to several volume replacements per second.

The pumpdown pressure which controls the oxygen concentration may be from about 0.1 to 100, preferably, about 5 to 50 millitorr. Depending on the capacity of the pump, these pumpdown pressures may be reached in about 1 min. to 72 hours.

The polymeric surface of the invention modified by exposure to a plasma generated from an ammonia oxygen mixture contains amino groups bonded onto its surface. In addition, oxygen containing groups, such as carbonyl, carboxyl, hydroxyl, ether and peroxide groups are present consequent to reaction of the surface with reactive oxygen species.

In the following examples, polymeric substrates are subjected to a plasma generated from an oxygen-ammonia mixture. The plasma-treated substrate surfaces may be examined by conventional electron spectroscopy for chemical analysis (ESCA), to measure binding energy shifts and determine therefrom the nature of the functional groups on the surface. Comparative ESCA data for the plasma modified surfaces of the invention and untreated surfaces are given in Table I.

The amino and oxygen-containing groups introduced onto the substrate surface by the plasma render the surface amenable to the deposition and adherence of cells. In the second step of the method of the invention, any of a variety of cell types may be applied to the plasma treated surfaces of the invention. Suitable cell types are generally epithelial-like. The most preferred cells for application to the plasma treated surface are endothelial cells. Methods to isolate and purify endothelial cells from various sources are well known, and the provision of cells for adherence to the plasma-treated substrate surface of the invention is not part of the invention.

Endothelialization may be carried out by contacting the plasma-treated substrate surface with sufficient cells suspended in a medium to cause formation of an adhered confluent layer without a requirement for cell proliferation. In accordance with the invention, this technique and the suspending medium are referred to as sodding and the sodding medium respectively.

Any sodding medium which is not deleterious to the cells may be used. Preferred sodding media are buffers, as for example, buffered saline. The cells adhere confluently in a manner of minutes, generally in about 1 to 60 minutes. If desired, adherence may be hastened by incubating the sodded surface at a temperature of from about 10° to 50° C., preferably at 37° C.

The number of cells required to sod the plasma-treated surface varies somewhat in accordance with the particular polymer and the particular surface chemistry after plasma treatment. In general about $10^5$ cells per square centimeter of surface to be covered is sufficient, but a greater concentration may also be used. Determination of this number and the concentration of cells in the sodding medium, which is not critical, are well within the purview of one skilled in the art. Likewise, determination of cell adherence and confluency by scanning electron microscopy or light microscopy after staining are conventional.

In another aspect of the invention, antithrombogenic articles having a plasma-treated surface and a confluent layer of endothelial cells adhered directly to the plasma-treated surface are provided. Exemplary of articles contemplated to fall within the scope of the invention are prosthetic devices which come into contact with blood, and include, as non-limiting examples, artificial hearts, heart valves, pins and preferably, vascular grafts. The most preferred article of the invention is a small diameter vascular graft, such as a conduit of inside diameter of 6 mm or less having a plasma-treated and endothelialized lumen wall.

EXAMPLE I

Flat polyurethane film samples were modified in an RF plasma discharge system. A pair of 8 inch diameter aluminum electrodes spaced 3¾ inches apart were used inside a 12 inch diameter 22 inch tall vacuum chamber. RF power was delivered from a variable frequency oscillator/amplifier pair into a "T" matching network, through a balun transformer into the vacuum chamber using a sealed feedthrough, and then the balanced lines were connected to the opposing horizontal electrodes. The film samples were placed atop the lower electrode.

The chamber was pumped down to 60 mTorr over a period of 6 minutes. While continuing to pump, anhydrous ammonia gas was bled through a fine metering valve into the chamber at a rate sufficient to maintain a 200 mTorr pressure. After thus purging the system for 1 minute, a 10.5 MHz 25 watt RF plasma was produced for 2 minutes to treat the film. Following treatment, the system was vented to atmosphere and the samples removed.

The surface chemistry of the samples was measured using ESCA and the resulting elemental compositions for treated and untreated samples are given in Table 1.

TABLE I

| | Elemental Atomic Percent Values for Plasma Treated and Virgin Polyurethanes | | | | | |
|---|---|---|---|---|---|---|
| | Plasma Treated | | | Virgin Polymer | | |
| Substrate | Carbon | Oxygen | Nitrogen | Carbon | Oxygen | Nitrogen |
| Polyurethane I | 71 | 18 | 7 | 83 | 12 | 3.9 |
| Polyurethane II | 77 | 12 | 9.3 | 91 | 4.5 | 4.2 |

TABLE I-continued

| | Elemental Atomic Percent Values for Plasma Treated and Virgin Polyurethanes | | | | | |
|---|---|---|---|---|---|---|
| | Plasma Treated | | | Virgin Polymer | | |
| Substrate | Carbon | Oxygen | Nitrogen | Carbon | Oxygen | Nitrogen |
| Polyurethane III | 72 | 18 | 7.7 | 74 | 20 | 5.1 |
| Polyurethane IV | 67 | 19 | 11 | 76 | 20 | 3.9 |
| Polyurethane V | 72 | 14 | 7.9 | 86 | 8.2 | 3.6 |

EXAMPLE II

PLASMA TREATMENT OF A SMALL DIAMETER POLYSTYRENE CONDUIT

The inside wall of a section of polystyrene tubing 15 cm long and a 2.5 mm inside diameter was subjected to a plasma generated in the plasma generator of the aforesaid copending application. Conditions of plasma treatment were similar to those used in Example I except that a 11.4 MHz 75 watt RF plasma was used and ammonia gas pressure was maintained at 14 Torr. Treatment duration was 25 seconds.

EXAMPLE III

PLASMA TREATMENT OF A SMALL DIAMETER POLYURETHANE CONDUIT

The inside wall of a section of polyurethane conduit 100 cm long and 3.5 mm inside diameter was plasma modified as described in Example II.

EXAMPLE IV

GENERAL PROCEDURE FOR DEPOSITION OF ENDOTHELIAL CELLS ONTO A POLYMER SURFACE

A plasma treated polymer film was cut into disks having an area of 2 cm$^2$, and the disks were placed into the wells of a FALCON TM 24-well tissue culture plate. A series of experimental controls was also prepared by adding one milliliter of 1% gelatin to each of six wells and one ml of 0.9% saline to six other wells. One ml of 0.9% saline was added to each well containing a plasma treated polymer disk. Both 24-well plates were covered with parafilm and maintained at 4° C. for 24 hours to ensure adequate hydration of test and control surfaces.

The gelatin and saline solutions were removed by aspiration and 0.8 ml of a stock suspension containing 2.5×10$^5$ endothelial cells per ml was added to the wells. The cells were incubated for one hour at 37° C. in a 5% carbon dioxide atmosphere, then washed with buffer and decanted using trypsin. The test surfaces and controls were washed again and the adherent cells were stained with hematoxylin. The number of adherent cells was determined using standard light microscopy techniques.

The results of this experiment are given in Table II as adherent endothelial cell population density, in cells per cm$^2$ for a variety of plasma treated polymer formulations.

TABLE II

| Endothelial Cell Adherence to Plasma Treated Polymer Disks | |
|---|---|
| Polymer* | Adherent Cell Density (cells/cm$^2$) |
| Polyethylene Terephthalate | |
| sample PET-1 | 15800 |
| sample PET-2 | 31000 |
| Polystyrene | |
| sample PS-1 | 44200 |
| sample PS-2 | 30200 |
| Polyurethane | |
| sample PU-1 | 25200 |
| sample PU-2 | 35700 |
| sample PU-3 | 46800 |
| sample PU-4 | 34500 |
| sample PU-5 | 30700 |
| Polyolefin | |
| sample PO-1 | 19700 |
| sample PO-2 | 60500 |
| sample PO-3 | 64800 |
| sample PO-4 | 14200 |
| Saline Control | 12600 |
| Gelatin Control | 40100 |

*Each polymer sample represents a different polymer formulation.

EXAMPLE V

EFFECT OF PLASMA TREATMENT OF THE ADHERENCE OF PRIMARY ENDOTHELIAL CELLS

Following the general procedure for deposition of endothelial cells onto a polymer surface described in Example IV, an inoculum of primary human endothelial cells was applied to plasma treated and virgin polyurethane disk samples. Two polyurethane types were examined, with cell adherence results shown in Table III. While primary endothelial cells do not exhibit the same propensity for attachment to polymer surfaces as cultured endothelial cells, the relative affinity for plasma treated polymer surfaces is higher than for untreated virgin polymer surfaces.

TABLE III

| Primary Endothelial Cell Adherence to Plasma Treated and Virgin Polyurethane | |
|---|---|
| Polymer | Adherent Cell Density (cells/cm$^2$) mean ± standard deviation |
| Polyurethane A | |
| plasma treated | 14606 ± 7211 |
| untreated virgin | 6287 ± 2183 |
| Polyurethane B | |
| plasma treated | 15058 ± 7607 |
| untreated virgin | 7005 ± 5301 |

EXAMPLE VI

DEPOSITION OF CELLS ONTO THE INSIDE WALL OF A PLASMA

Treated Small Diameter Polyurethane Conduit

Polyurethane conduits of Example III with internal diameter of 3.5 mm were plasma treated using the conditions described in Examples I and II. A primary endothelial cell population was suspended in buffer as described in Example IV at an inoculation density of $2 \times 10^5$ endothelial cells per square centimeter of polymer surface area calculated for the internal lumen of the conduits.

Each tube was encased in a supporting glass tube with connecting ports into which the cell suspension and buffer were introduced. The tubes were divided into two groups for incubation. Group I was rotated axially at a constant rate of 360 per minute and Group II was rotated axially in increments of 90 every fifteen minutes. Both groups were incubated for one hour at 37° C. in a 5% carbon dioxide atmosphere. A gelatin control was also prepared according to the procedure of Example IV.

The cell adherence results appear in Table IV. Both methods of incubation allow endothelial cell adherence, however, a more uniform layer is achieved using the constant rotational method.

TABLE IV

Endothelial Cell Adherence to Plasma Treated Polyurethane Conduits

| Conduit Sample Number | Adherent Cell Density (cells/cm²) | |
|---|---|---|
| | Group I (constant rotation) | Group II (incremental rotation) |
| Sample 1 | 20753 | 22429 |
| Sample 2 | 34539 | 8211 |
| Sample 3 | 14595 | 19397 |
| Sample 4 | 21017 | 10414 |

Gelatin Control = 14652

What is claimed is:

1. A method for endothelialization of a polymeric surface comprising contacting a polymeric surface with a plasma generated from a gaseous material comprising nitrogen whereby said polymeric surface is modified to contain surface amino groups, and applying to said modified surface sufficient endothelial cells to form a confluent layer of cells on said amino group-containing surface without a requirement for cell proliferation.

2. The method in accordance with claim 1 wherein said surface is selected from the group consisting of polyurethane, polystyrene, polyester, polyolefin and fluorinated polyolefin.

3. The method in accordance with claim 1 wherein said surface is relatively flat.

4. The method in accordance with claim 1 wherein said surface is curved.

5. The method in accordance with claim 1 wherein said material further comprises a second material selected from the group consisting of hydrogen, halogen, argon, neon, krypton and xenon, oxygen and a compound of oxygen.

6. The method in accordance with claim 1 wherein said plasma is generated using a measured power density level of about 0.001 to 400 watts per cubic centimeter generated over a frequency range from DC to 100 megahertz, said plasma being applied to said material for about 2 seconds to 12 hours at about 0° to 200° C., the pressure of said material being about 0.01 to 100 torr.

7. The method in accordance with claim 1 wherein said applying includes incubating.

8. The method in accordance with claim 7 wherein said incubating is carried out at a temperature of from about 10° to 50° C. for 1 to 120 minutes.

9. A method for applying cells to a surface comprising contacting a surface with a plasma generated from a gas whereby said surface is modified to contain reactive functional groups from said gas and applying to said modified surface sufficient cells to form a confluent layer of cells on said surface containing said functional groups without a requirement for cell proliferation.

10. The method of claim 9 wherein said cells are epithelial cells.

11. The method in accordance with claim 9 wherein said surface is selected from the group consisting of an inorganic surface and a polymeric surface.

12. The method in accordance with claim 9 wherein said gas is selected from the group consisting of nitrogen, oxygen, and a compound thereof.

13. A method comprising treating the lumen wall of a polymeric conduit with a plasma generated from a gas, said plasma causing bonding of a reactive functional group from said gas onto said lumen wall; and sodding said lumen wall containing said reactive functional group with sufficient endothelial cells to form a confluent layer of cells adhered to said lumen wall without a requirement for cell proliferation.

14. The method of claim 13 wherein the lumen wall to be treated has an inside diameter of 4 mm or less.

15. The method in accordance with claim 13 wherein said gas is selected from the group consisting of oxygen, nitrogen and a compound thereof.

16. An antithrombogenic article comprising a plasma-treated polymeric surface having amino groups bonded thereto and a confluent layer of endothelial cells adhered to said surface having amino groups.

17. The article in accordance with claim 16 wherein said polymeric surface is selected from the group consisting of a polyolefin surface, a polyurethane surface, a fluorinated polyolefin surface, a polyester surface and a polystyrene surface.

18. The article in accordance with claim 16 selected from the group consisting of a plate, strip, film, sheet, fiber, fabric, conduit and cast.

19. An antithrombogenic article comprising a plasma-treated surface having reactive functional groups bonded thereto and a confluent layer of epithelial cells adhered to said surface containing reactive functional groups.

20. The article in accordance with claim 19 wherein said functional groups are selected from the group consisting of amino groups and groups containing oxygen.

21. A polymeric conduit having an inside diameter less than about 6 mm comprising a plasma-treated lumen wall, said wall having amino groups bonded thereto and a confluent layer of endothelial cells adhered to said lumen wall whereby said conduit is antithrombogenic.

* * * * *

UNITED STATES PATENT AND TRADEMARK OFFICE
CERTIFICATE OF CORRECTION

PATENT NO. : 4,927,676

DATED : May 22, 1990

INVENTOR(S) : J.L. Williams et al

It is certified that error appears in the above-identified patent and that said Letters Patent is hereby corrected as shown below:

Title page, item [75] should read as follows:

[75] Inventors: Joel L. Williams, David B. Montgomery, both of Cary; Lillian P. Baldwin, Durham, all of North Carolina and Joseph A. DiPisa, Jr., Wyckoff, New Jersey Signed and Sealed this Ninth Day of July, 1991

Attest:

HARRY F. MANBECK, JR.

Attesting Officer

Commissioner of Patents and Trademarks